United States Patent [19]

Breuner et al.

[11] 4,127,716
[45] * Nov. 28, 1978

[54] 3-HETEROTHIOMETHYL UREIDO CEPHALOSPORINS

[75] Inventors: Hermann Breuer; Uwe D. Treuner, both of Regensburg, Germany

[73] Assignee: E. R. Squibb & Sons, Inc., Princeton, N.J.

[*] Notice: The portion of the term of this patent subsequent to Dec. 7, 1993, has been disclaimed.

[21] Appl. No.: 764,134

[22] Filed: Feb. 2, 1977

Related U.S. Application Data

[63] Continuation-in-part of Ser. No. 664,796, Mar. 8, 1976, Pat. No. 4,088,816, and a continuation-in-part of Ser. No. 664,795, Mar. 8, 1976, Pat. No. 4,088,815, which is a continuation-in-part of Ser. No. 507,900, Sep. 20, 1974, abandoned, said Ser. No. 664,795, is a continuation-in-part of Ser. No. 507,900, Sep. 20, 1974, abandoned.

[51] Int. Cl.² .................. C07D 501/56; C07D 501/54; A61K 31/545
[52] U.S. Cl. ......................... 544/27; 544/26; 544/28; 544/30; 544/4; 424/246; 424/245
[58] Field of Search .................... 544/26, 27

[56] References Cited

U.S. PATENT DOCUMENTS

| | | | |
|---|---|---|---|
| 3,641,021 | 2/1972 | Ryan, Jr. | 260/243 C |
| 3,757,015 | 9/1973 | Crast, Jr. | 260/243 C |
| 3,759,904 | 9/1973 | Crast, Jr. | 260/243 C |
| 3,796,801 | 3/1974 | Guarini et al. | 424/246 |
| 3,813,388 | 5/1974 | Crast, Jr. | 260/243 C |
| 3,821,207 | 6/1974 | Chow et al. | 260/243 C |
| 3,860,591 | 1/1975 | Breuer | 260/243 C |
| 3,867,380 | 2/1975 | Dunn et al. | 260/243 C |
| 3,926,985 | 12/1975 | Breuer | 260/243 C |
| 3,996,217 | 12/1976 | Breuer et al. | 260/243 C |
| 4,088,815 | 5/1978 | Brewer et al. | 544/26 |
| 4,088,816 | 5/1978 | Treuner et al. | 544/27 |

Primary Examiner—Donald G. Daus
Assistant Examiner—Diana G. Rivers
Attorney, Agent, or Firm—Lawrence S. Levinson; Merle J. Smith; Stephen B. Davis

[57] ABSTRACT

L-Isomer compounds of the formula

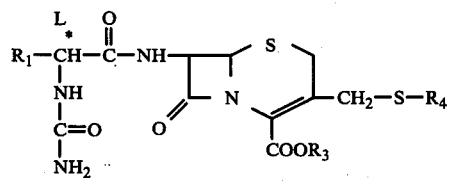

wherein $R_1$ is phenyl, thienyl or furyl; $R_4$ represents certain heterocyclic groups; $R_3$ is hydrogen, lower alkyl, phenyl-lower alkyl, substituted phenyl-lower alkyl, diphenyl-lower alkyl, tri(lower alkyl)stannyl, tri(lower alkyl)silyl, a salt forming ion, or the group

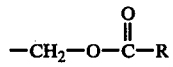

wherein R is lower alkyl, phenyl, phenyl-lower alkyl, or substituted phenyl and phenyl-lower alkyl are disclosed. These compounds are useful as antibacterial agents.

28 Claims, No Drawings

3-HETEROTHIOMETHYL UREIDO CEPHALOSPORINS

This application is a continuation-in-part of Ser. Nos. 664,796, and now U.S. Pat. 4,088,816 and 664,795, and now U.S. Pat. 4,088,815, both filed on Mar. 8, 1976. Ser. No. 664,796 is a continuation-in-part of Ser. No. 507,900 filed on Sept. 20, 1974, now abandoned, and Ser. No. 664,795 is a continuation-in-part of Ser. No. 507,906 filed on Sept. 20, 1974, now abandoned.

BACKGROUND OF THE INVENTION

Cephalosporins having an α-ureido acyl side chain and 3-position substituents other than heterothiomethyl are disclosed by Erickson in U.S. Pat. No. 3,673,183, by Welch et al. in U.S. Pat. No. 3,708,479, and by Dolfini et al. in U.S. Pat. No. 3,833,568. Cephalosporins having an α-ureido acyl side chain and a heterothiomethyl group in the 3-position are described as starting materials in the preparation of various acylthiomethyl esters by Breuer in U.S. Pat. No. 3,860,591, Cephalosporins having an α-ureido acyl side chain and a triazolylthiomethyl group and an oxopyridazinylthiomethyl group in the 3-position are disclosed by Breuer et al. in U.S. Pat. Nos. 3,996,217 and 3,996,218.

7α-methoxy cephalosporins having an α-ureido acyl side chain and a heterothiomethyl group in the 3-position are disclosed by Dolfini in U.S. Pat. Nos. 3,978,051; 3,989,693; 3,989,697; and 4,000,134.

Cephalosporins having an α-acylureido acyl side chain and a heterothiomethyl group in the 3-position are disclosed by Cooper et al. in U.S. Pat. No. 3,925,368 and German Offenlegungsschrift No. 2,514,019, of Cooper in U.S. Pat. No. 3,956,292, and by Kocsis et al. in U.S. Pat. No. 3,954,802.

Cephalosporins having various heterothiomethyl groups in the 3-position and α-amino acyl side chains are disclosed as possessing antibacterial activity in U.S. Pat. Nos. 3,641,021; 3,759,904; 3,813,388; 3,821,207; 3,878,204; 3,796,801 (method of treating Enterobacter infections), etc. Also disclosed as useful intermediates are cephalosporins, substituted in the 3-position with —CH$_2$—S—hetero groups and in the 7-position with a

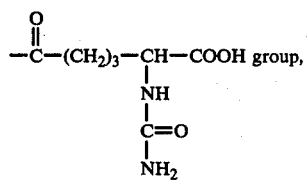

U.S. Pat. No. 3,819,621.

SUMMARY OF THE INVENTION

This invention relates to the optically active L-isomer form of the cephalosporins of the formula

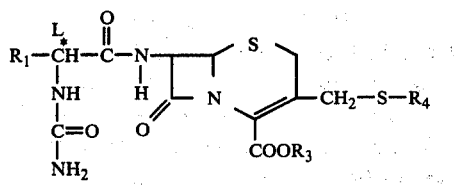

(I)

wherein R$_1$ is phenyl, thienyl, or furyl; R$_4$ represents certain heterocyclic group; and R$_3$ represents hydrogen, lower alkyl, phenyl-lower alkyl, diphenyl-lower alkyl, substituted phenyl-lower alkyl, tri(lower alkyl) stannyl, tri(lower alkyl) silyl, a salt forming ion, or the group

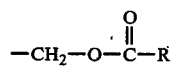

wherein R is lower alkyl, phenyl, phenyl-lower alkyl, or substituted phenyl and phenyl-lower alkyl.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 8 carbon atoms, preferably 1 to 4 carbons. Examples of the type of groups contemplated are methyl, ethyl, propyl, isopropyl, butyl, t-butyl, etc. The lower alkoxy groups include such lower alkyl groups attached to an oxygen, e.g., methoxy, ethoxy, propoxy, etc. The phenyl-lower alkyl and diphenyl-lower alkyl groups include such lower alkyl groups attached to a phenyl, e.g., benzyl, phenethyl, diphenylmethyl, etc.

The substituted phenyl and substituted phenyl-lower alkyl groups include one or two (preferably only one) simple substituents selected from halogan (preferably chlorine or bromine), lower alkyl and lower alkoxy, e.g. 2-, 3- or 4-chlorophenyl, 2-, 3-. pr 4-bromophenyl, 3,4-dichlorophenyl, 2-methylphenyl, 4-ethoxyphenyl, 2-, 3-, or 4-chlorobenzyl, 2-, 3-, or 4-ethylphenethyl, etc.

The salt forming ions represented by R$_3$ may be metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine.

The heterocyclic groups represented by R$_4$ are

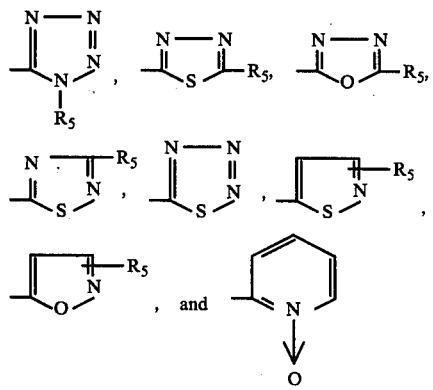

wherein
R$_5$ is hydrogen or alkyl of 1 to 4 carbons.

The preferred embodiments of this invention are the compounds of formula I wherein:

$R_3$ is hydrogen, sodium or potassium.

$R_4$ is

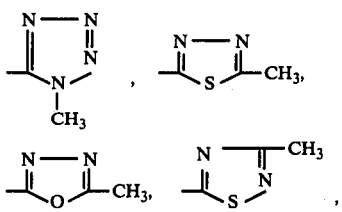

especially 5-methyl-1,3,4-thiadiazol-2-yl and 1-methyl-1H-tetrazol-5-yl.

The L-isomer compounds of formula I are preferably prepared by reacting an α-amino compound of the formula

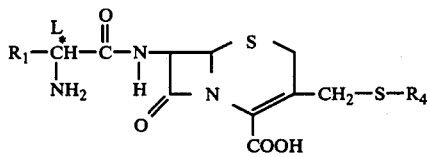

(II)

preferably in the form of its trifluoroacetic acid salt with an alkali or alkaline earth cyanate such as potassium cyanate in solution at a pH of from about 7 to about 8.

The compounds of formula II can be prepared by acylating a 3-heterothiomethyl-7-aminocephalosporin of the formula

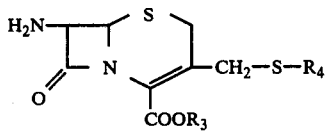

(III)

wherein $R_3$ is preferably diphenylmethyl or t-butyl or other ester protecting groups with an acid chloride of the formula

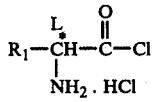

or an α-(substituted)amino acid of the formula

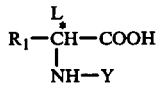

(V)

wherein Y is a protecting group such as

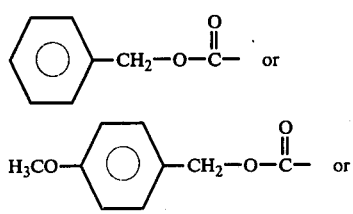

-continued

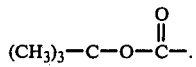

The protecting group is removed, for example, by treatment with trifluoroacetic acid and anisole to yield the trifluoroacetate salt of the compound of formula II.

The L-isomer compounds of formula I can also be prepared by reacting an α-ureido compound of the formula

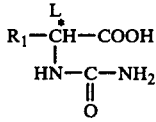

(VI)

with the 3-heterothiomethyl-7-aminocephalosporin of formula III.

This reaction is carried out by converting the α-ureido compound of formula VI to a mixed carbonic or other anhydride by treating a solution of the α-ureido compound in an organic solvent containing a tri(lower alkyl)amine with an anhydride forming agent, i.e. a lower alkyl chloroformate, an aryl chloroformate, or an acyl halide, at reduced temperature of from about 0° C to about −20° C.

Alternatively, the α-ureido compound of formula VI can be converted to an activated ester by reacting with a carboxyl group activating agent such a dicyclohexylcarbodiimide or bisimidazole carbonyl. In some cases the carboxyl group may be activated by conversion to an acid halide, e.g., the chloride, or to an azide.

The L-isomers of formula I can also be prepared by reacting the compound of formula VI with 7-ACA preferably in the presence of dicyclohexylcarbodiimide to yield the compound of formula VII (as disclosed in U.S. Pat. No. 3,833,568)

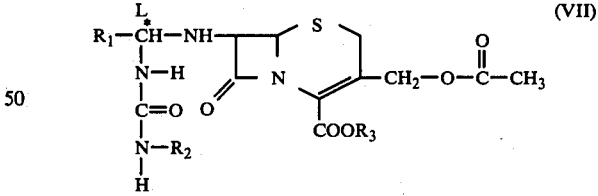

(VII)

followed by treatment with the compound of the formula

(VIII)

in solution at a pH of from about 7.8 to about 8.0.

Similarly, the L-isomers of formula I can be prepared by reacting the compounds of formula IV or V with an ester of 7-ACA preferably in the presence of dicyclohexylcarbodiimide followed by treatment with an acid (HX), preferably trifluoroacetic acid in the presence of anisole, to yield the salt of formula

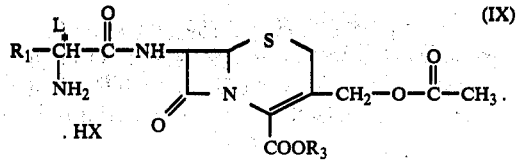

(IX)

The salt of formula IX is then treated with an alkali or alkaline earth cyanate followed by treatment with the compound of formula VIII to yield the desired compounds.

The compounds of formula I wherein $R_3$ is lower alkyl, phenyl-lower alkyl, substituted phenyl-lower alkyl, diphenyl-lower alkyl, or the acyloxymethyl group

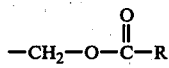

may be obtained by reacting the 3-heterothiomethyl-7-amino-cephalosporin of formula III or the 7-ACA either before or after the acylation of the 7-amino substituent with one or two moles of a compound of the formula halo-$R_3$                (X)

or $R_3=N^+=N^-$             (XI)

wherein halo is preferably chlorine or bromine in an inert solvent such as dimethylformamide, acetone, dioxane, benzene, or the like at about or below ambient temperature.

Similarly, the compounds of formula I wherein $R_3$ is tri(lower alkyl)stannyl or tri(lower alkyl)silyl are obtained by introducing such groups onto the 3-heterothiomethyl cephalosporanic acid moiety either before or after the acylation reaction.

The carboxylate salts of the compounds of formula I are formed by reacting the carboxyl group of the cephalosporanic acid moiety, i.e. $R_3$ is hydrogen, with any of the salt forming ions described above.

The L-isomer compounds of formula I have a broad spectrum of antibacterial activity against both gram positive and gram negative organisms such as *Staphylococcus aureus, Salmonella schottmuelleri, Klebsiella pneumoniae, Proteus rettgeri, Escherichia coli*, etc. In particular, it has been found that these L-isomers are considerably more active than the corresponding D-isomer or D,L-isomeric mixture against beta-lactamase producing organisms such as Enterobacter, indole-positive Proteus, resistant *Escherichia coli*, and Serratia.

The compounds of formula I can be used as antibacterial agents to combat infections due to organisms such as those named above, and in general may be utilized in a manner similar to cephalothin and other cephalosporins. For example, a compound of formula I or a physiologically acceptable salt thereof may be used in various animal species in an amount of about 1 to 100 mg./kg., daily, orally or parenterally, in single or two to four divided doses to treat infections of bacterial origin, e.g., 5.0 mg./kg. in mice.

Up to about 600 mg. of a compound of formula I or a physiologicaly acceptable salt thereof may be incorporated in an oral dosage form such as tablets, capsules or elixirs or in an injectable form in a sterile aqueous vehicle prepared according to conventional pharmaceutical practice.

Illustrative process details are provided in the examples for the various reactions. All temperatures are on the centigrade scale.

EXAMPLE 1

7β-[[[(Aminocarbonyl)amino](L-2-thienyl)acetyl-]amino]-3-[[(1-methyl-1H-tetrazol-5-yl)thio]methyl]-8-oxo-5-thia-1-azabicyclo[4.2.0]oct-2-ene-2-carboxylic acid a.

L-α-[[[(4-Methoxyphenyl)methoxy]amino]-2-thiopheneacetic acid -[( 14.2 g. of L-(2-thienyl)glycine (prepared by the method of Nishimura et al., Nippon Kagaku Zasshi, Vol. 82, p. 1688-91 (1961); Chem. Abst., Vol. 58, p. 11464f) are suspended in 142 ml. of water and brought into solution by the addition of 37.9 ml. of triethylamine. A solution of 20.6 g. of (p-methoxyphenyl)methoxycarbonylazide in 142 ml. of dioxane is added with stirring. The mixture which is turbid at first becomes clear after 30 minutes. This is stirred for an additional hour at room temperature. The dioxane is then evaporated in vacuum. Flakes form in the aqueous phase which are extracted by shaking with ether. The aqueous phase is cooled to 0°, layered over with ethyl acetate and acidified with 2N hydrochloric acid to pH 2.5. The aqueous phase is extracted twice more with ethyl acetate, the combined ethyl acetate extracts are dried with magnesium sulfate and concentrated in vacuum to 23.5 g. of L-α-[[[A(4-methoxyphenyl)methoxy]carbonyl-]amino]-2-thiopheneacetic acid; m.p. 100°-102°; $[α]_D^{20} = +68.3°$ (C=1, tetrahydrofuran).

b.

7β-[[[[(4-Methoxyphenyl)methoxy]carbonyl-]amino](L-2-thienyl)-acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 14.9 g. of 3-[(1-methyl-1H-tetrazol-5-yl)thio]-7-amino-cephalosporanic acid, diphenylmethyl ester are dissolved in 300 ml. of methylene chloride and 300 ml. of anhydrous tetrahydrofuran are added. Then 11.62 g. of L-α-[[[(4-methoxyphenyl)-methoxy]carbonyl-]amino]-2-thiopheneacetic acid from part (a) are added, the mixture is cooled to 0°, and a solution of 6.79 g. of dicyclohexylcarbodiimide in 100 ml. of anhydrous tetrahydrofuran is added dropwise with stirring over 30 minutes. The reaction mixture is stirred for 90 minutes at 0-5° and 90 minutes at room temperature. The precipitated dicyclohexylurea is then filtered off and the filtrate is concentrated in vacuum. The residue is taken up with ethyl acetate, filtered, washed with sodium bicarbonate solution and with water. The ethyl acetate solution is dried with magnesium sulfate, treated with activated charcoal, filtered and concentrated in vacuum to a small volume. On stirring in excess petroleum ether, 24 g. of 7α-[[[[[(4-methoxyphenyl)methoxy]carbonyl-]amino]-(L-2-thienyl)acetyl]amino]-3-[[(1-methyl-1H-tetrazol-5-yl)-thio]methyl]-8-oxo-5-thia-1-azabicyclo[4.2.0]oct-2-ene-2-carboxylic acid, diphenylmethyl ester; m.p. 110°; are obtained as a precipitate.

c.
7β-[[(α-Amino-L-2-thienyl)acetyl]amino]-3-[[(1-methyl-1H-tetrazol-5-yl)thio]methyl]-8-oxo-5-thia-1-azabicyclo[4.2.0]-oct-2-ene-2-carboxylic acid, trifluoroacetic acid salt 24 g. of the diphenylmethyl ester product from part (b) are stirred in 100 ml. of anisole and 300 ml. of trifluoroacetic acid are added dropwise at 0°. After 10 minutes, this mixture is evaporated under vacuum. The residue is treated with ether and filtered to yield 17.8 g. of 7β-[[(α-amino-L-2-thienyl)-acetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt.

d.
7β-[[[(Aminocarbonyl)amino](L-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid 12 g. of the trifluroacetic acid salt product from part (c) are added to a solution of 3.4 g. of potassium cyanate in 85 ml. of water and stirrer for 3 hours at room temperature. This mixture is filtered and the filtrate is acidified to pH 1.5 with 2N hydrochloric acid while cooling. The precipitate is isolated and yields 6.8 g. of 7β-[[[(amino-carbonyl)amino](L-2-thienyl)acetyl]amino]-3-[[(1-methyl-1H-tetrazol-5-yl)thio]methyl]-8-oxo-5-thia-1-azabicyclo[4.2.0]-oct-2-ene-2-carboxylic acid; m.p. 149°-153° (dec.).

An aqueous equimolar solution of this acid and sodium bicarbonate is lyophilized to yield 7β-[[[(aminocarbonyl)amino]-(L-2-thienyl)acetyl]amino]-3-[[(1-methyl-1H-tetrazol-5-yl)thio]-methyl]-8-oxo-5-thia-1-azabicyclo[4.2.0]oct-2-ene-2-carboxylic acid, sodium salt; m.p. 187°-188° (dec.). In a similar manner, one can obtain the potassium salt.

EXAMPLE 2

7β-[[[(Aminocarbonyl]amino](L-3-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid a.
L-α-[[[(4-Methoxyphenyl)methoxy]carbonyl]amino]-3-thiophenacetic acid 18 g. of L-(3-thienyl)glycine (prepared by the method of Nishimura et al., supra) are suspended in 300 ml. of water with 10 g. of magnesium oxide. 32 g. of (p-methoxyphenyl)-methoxycarbonylazide in 250 ml. of dioxane are added dropwise. The mixture is stirred for 24 hours at room temperature, then the dioxane is distilled off. The residue is filtered and the filtrate is extracted by shaking with ether. The aqueous phase is layered with ethyl acetate and acidified to pH 2.5 with 2N hydrochloric acid with cooling. The ethyl acetate is washed with water, dried over sodium sulfate and evaporated. The residual oil is dissolved in toluene, cyclohexane is added, and the mixture is refrigerated. Crystallization begins and 20.8 g. of white crystalline L-α-[[[(4-methoxyphenyl)methoxy]carbonyl]-amino]-3-thiopheneacetic acid are obtained; m.p. 95°-97°: $[\alpha]_D^{25} = +76.8°$ (0.1% in methanol).

b.
7β-[[[[[(4-Methoxyphenyl)methoxy]carbonyl]amino](L-3-thienyl)-acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 10 g. of the L-α-[[[(4-methoxyphenyl)methoxy]carbonyl]-amino]-3-thiopheneacetic acid from part (a) are dissolved in 150 ml. of tetrahydrofuran and stirred for 15 minutes at 0° with 6.5 g. of dicyclohexylcarbodiimide. Then 14 g. of 3-[(1-methyl-1H-tetrazol-5-yl)thio]-7-aminocephalosporanic acid, diphenylmethyl ester dissolved in 100 ml. of tetrahydrofuran are added. After 12 hours, the reaction mixture is filtered, the filtrate is treated with charcoal and evaporated in vacuum. The residual brown oil is dissolved in 20 ml. of methylene chloride and added dropwise to a mixture of ether and petroleum ether. 20 g. of light yellow 7β-[[[[[(4-methoxyphenyl)methoxy]carbonyl]amino](L-3-thienyl)-acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester are obtained; m.p. 95°.

c.
7β-[[(α-Amino-L-3-thieyl)acetyl]amino]-3-[[(1-methyl-1H-tetrazol-5-yl)thio]methyl]-8-oxo-5-thia-1-azabicyclo[4.2.0]-oct-2-ene-2-carboxylic acid, trifluoroacetic acid salt 13 g. of the diphenylmethyl ester product from part (b) are dissolved in 200 ml. of anisole-trifluoroacetic acid (1:4) at 5°. After 10 minutes stirring, the mixture is evaporated under vacuum. The residue is treated with a mixture of ether and petroleum ether and filtered to yield 8.4 g. of solid yellow 7β-[[(α-amino-L-3-thienyl-)acetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt; m.p. 125° (dec.).

d.
7β-[[[(Aminocarbonyl)amino](L-3-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid 7.9 g. of the trifluoroacetic acid salt product from part (c) are dissolved in 50 ml. of water and the pH is adjusted to 7.2 with 2N sodium hydroxide. After the addition of 1.5 g. of potassium cyanate, the mixture is stirred for 3 hours at constant pH. The reaction mixture is cooled, adjusted to pH 1.5 with 2N hydrochloric acid, the precipitate is filtered off and dissolved in methanol, then treated with charcoal. Concentrating the methanolic solution crystallizes 4.2 g. of 7β-[[[(aminocarbonyl-)amino](L-3-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid; m.p. 157° (dec.).

An equimolar solution of this acid and potassium bicarbonate is lyophilized to obtain as a yellow powder 7β-[[[(aminocarbonyl)amino](L-3-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid, potassium salt; m.p. 174° (dec.). In a similar manner, by employing sodium bicarbonate, one obtains the sodium salt.

EXAMPLE 3

7β-[[[(Aminocarbonyl)amino](L-phenyl)acetyl]amino]-3-[[(1-methyl-1H-tetrazol-5-yl)thio]methyl]-8-oxo-5-thia-1-azabicyclo-[4.2.0]oct-2-ene-2-carboxylic acid a.

L-α-[[[(4-Methoxyphenyl)methoxy]carbonyl]amino]-phenylacetic acid ]

L-Phenylglycine (obtained from D,L-phenylglycine by the method of Nishimura et al., supra) and magnesium oxide are suspended in water and reacted with a solution of (p-methoxyphenyl)methoxycarbonylazide in dioxane according to the procedure of example 1(a) to yield L-α-[[[(4-methoxyphenyl)methoxy]-carbonyl]amino]phenylacetic acid.

b.

7β-[[[[[(4-Methoxyphenyl)methoxy]carbonyl]amino](L-phenyl)-acetyl]amino]-3-[[(1-methyl-1H-tetrazol-5-yl)thio]methyl]-8-oxo-5-thia-1-azabicyclo[4.2.-0]oct-2-ene-2-carboxylic acid, diphenylmethyl ester 7-Amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester and L-α-[[[(4-methoxyphenyl)methoxy]carbonyl]-amino]phenylacetic acid from part (a) are reacted in the presence of dicyclohexylcarbodiimide according to the procedure of example 1(b) to yield 7β-[[[[[(4-methoxyphenyl)methoxy]-carbonyl]amino](L-phenyl)acetyl]amino]-3-[[(1-methyl-1H)tetrazol-5-yl)thio]methyl]-8-oxo-5-thia-1-azabicyclo[4.2.0]-oct-2-ene-2-carboxylic acid, diphenylmethyl ester; m.p. 117° (dec.).

c.

7β-[[(α-Amino-L-phenyl)acetyl]amino]-3-[[(1methyl-1H-tetrazol-5-yl)thio]methyl]-8-oxo-5-thia-1-azabicyclo acid, trifluoroacetic acid salt The diphenylmethyl ester product from part (b) is treated with trifluoroacetic acid and anisole according to the procedure of example 1(c) to yield 7β-[[(α-amino-L-phenyl)-acetyl]amino]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt.

d.

7β-[[[(Aminocarbonyl)amino](L-phenyl)acetyl]amino]-3-[[(1-methyl-1H-tetrazol-5-yl)thio]methyl]-8-oxo-5-thia-1-azabicyclo[4.2.0]oct-2-ene-2-carboxylic acid The trifluoroacetic acid salt product from part (c) is reacted with potassium cyanate according to the procedure of example 1(d) to yield 7β-[[[(aminocarbonyl)amino](L-phenyl)-acetyl]amino]-3-[[(1-methyl-1H-tetrazol-5-yl)thio]methyl]-8-oxo-5-thia-1-azabicyclo[4.2.-0]oct-2-ene-2-carboxylic acid; m.p. 156° (dec.).

An aqueous equimolar solution of this acid and potassium bicarbonate is freeze-dried to yield 7β-[[[(aminocarbonyl)-amino](L-phenyl)acetyl]amino]-3-[[(1-methyl-1H-tetrazol-5-yl)-thio]methyl]-8-oxo-5-thia-1-azabicyclo[4.2.0]oct-2-ene-2-carboxylic acid, potassium salt; m.p. 174° (dec.).

Similarly, by substituting sodium bicarbonate for the potassium bicarbonate one obtains the corresponding sodium salt.

EXAMPLE 4

7β-[[[(Aminocarbonyl)amino](L-2-furyl)acetyl]amino]-3-[[(1-methyl-1H-tetrazol-5-yl)thio]methyl]-8-oxo-5-thia-1-azabicyclo-[4.2.0]oct-2-ene-2-carboxylic acid a.

L-α-[[[(4-Methoxyphenyl)methoxy]carbonyl]amino]-2-furanacetic acid 40 g. of L-(2-furyl)glycine (obtained from D,L-(2-furyl)-glycine by the method of Nishimura et al., supra) are stirred into 455 ml. of water and brought into solution by the addition of 122 ml. of triethylamine. A solution of 66 g. of (p-methoxyphenyl)-methoxycarbonylazide in 455 ml. of dioxane is added with stirring. The turbid mixture becomes clear after 30 minutes reaction time and the dioxane is evaporated in vacuo. The aqueous phase is washed with ether, cooled to 0°, layered over with ethyl acetate and acidified to pH 2.5 with 2N hydrochloric acid. This mixture is extracted twice with ethyl acetate, the combined ethyl acetate extracts are dried with magnesium sulfate and concentrated in vacuo. The oily residue solidifies upon trituration with petroleum to yield 74 g. of L-α-[[[(4-methoxyphenyl)-methoxy]carbonyl]amino]-2-furanacetic acid; m.p. 91°–95° (dec.).

b.

7β[[[[[(4-Methoxyphenyl)methoxy]carbonyl]amino](L-2-furyl)-acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 36.4 g. (0.074 moles) of 3-[(1-methyl-1H-tetrazol-5-yl)-thio]-7-aminocephalosporanic acid, diphenylmethyl ester are dissolved in 370 ml. of methylene chloride. Then a solution of 27 g. (0.088 moles) of L-α-[[[(4-methoxyphenyl)methoxy]-carbonyl]amino]-2-furanacetic acid, from part (a), in 450 ml. of tetrahydrofuran is added, the mixture is cooled to 0°, and a solution of 16.73 g. (0.081 moles) of dicyclohexylcarbodiimide in 150 ml. of tetrahydrofuran is added dropwise. The mixture is stirred for 90 minutes at 0° and 90 minutes at room temperature. The precipitated dicyclohexylurea is filtered off under suction and the filtrate is concentrated. The residue is taken up in ethyl acetate, washed three times with sodium bicarbonate solution and three times with water, dried and concentrated. The concentrated residue solidifies upon trituration with ether. This material is filtered under suction and stirred in 250 ml. of ethyl acetate. The mixture is stirred for 2 hours at 0° and filtered under suction to yield 30.4 g. of 7 β-[[[[[(4-methoxyphenyl)methoxy]carbonyl]amino](L-2-furyl)-acetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester, m.p. 149°–152°.

c.

7β-[[(α-Amino-L-2-furyl)acetyl]amino]-3-[[(1-methyl-1H-tetrazol-5-yl)thio]methyl]-8-oxo-5-thia-1-azabicyclo[4.2.0]-oct-2-ene-2-carboxylic acid, trifluoroacetic acid salt 30 g. of the diphenylmethyl ester product from part (b) are treated with 120 ml. of anisole and 390 ml. of trifluoroacetic acid according to the procedure of example 1(c) to yield 21.9 g, of 7β-[[(α-amino-L-2-furyl)-acetyl]amino]-3-[[(1-methyl-1H-tetrazol-5-yl)thio]methyl]-8-oxo-5-thia-1-azabicyclo[4.2.0]-oct-2-ene-2-carboxylic acid, trifluoroacetic acid salt; m.p. 133°–135° (dec.).

d.

7β-[[[(Aminocarbonyl)amino](L-2-furyl)acetyl]amino]-3-[[(1-methyl-1H-tetrazol-5-yl)thio]methyl]-8-oxo-5-thia-1-azabicyclo-[4.2.0]oct-2-ene-2-carboxylic acid

28.2 g. of the trifluoroacetic acid salt product from part (c) are suspended in 290 ml. of water at room temperature. 8.15 g. of potassium cyanate are added and the mixture is stirred for 3 hours at room temperature. The almost clear solution is cooled to 0°–5° and acidified to pH 3.5. A flocculent precipitate is filtered off. The clear filtrate is acidified to pH 1.5 and allowed to stand in the refrigerator at about 0°–5° to yield 19.8 g of 7β-[[[(aminocarbonyl)amino](L-2-furyl)-acetyl]amino]-3-[[(1-methyl-1H-tetrazol-5-yl)thio]methyl]-8-oxo-5-thia-1-azabicyclo[4.2.0]oct-2-ene-2-carboxylic acid; m.p. 142°–145° (dec.).

An aqueous equimolar solution of this acid and sodium bicarbonate is lyophilized to yield 7β-[[[(aminocarbonyl)amino]-(L-2-furyl)acetyl]amino]-3-[[(1-methyl-1H-tetrazol-5-yl)thio]-methyl]-8-oxo-5-thia-1-azabicyclo[4.2.0]oct-2-ene-2-carboxylic acid, sodium salt; m.p. 170°–174° (dec.). In a similar manner by employing potassium bicarbonate one obtains the potassium salt.

EXAMPLE 5

7β-[[[(Aminocarbonyl)amino](L-3-furyl)acetyl]amino]-3-[[(1-methyl-1H-tetrazol-5-yl)thio]methyl]-8-oxo-5-thia-1-azabicyclo-[4.2.0]oct-2-ene-2-carboxylic acid

Following the procedure of example 4 but substituting L-(3-furyl)glycine (obtained from D,L-(3-furyl)glycine by the method of Nishimura et al., supra) for the L-(2-furyl)-glycine in part (a), one obtains 7β-[[[(aminocarbonyl)amino](L-3-furyl)acetyl]amino]-3-[[(1-methyl-1H-tetrazol-5-yl)thio]methyl]-8-oxo-5-thia-1-azabicyclo[4.2.0]oct-2-ene-2-carboxylic acid and its sodium and potassium salts.

EXAMPLES 6–55

Following the procedure of example 1 but employing the substituted 7-aminocephalosporanic acid derivatives shown in Col. A the products shown in Col. B are obtained.

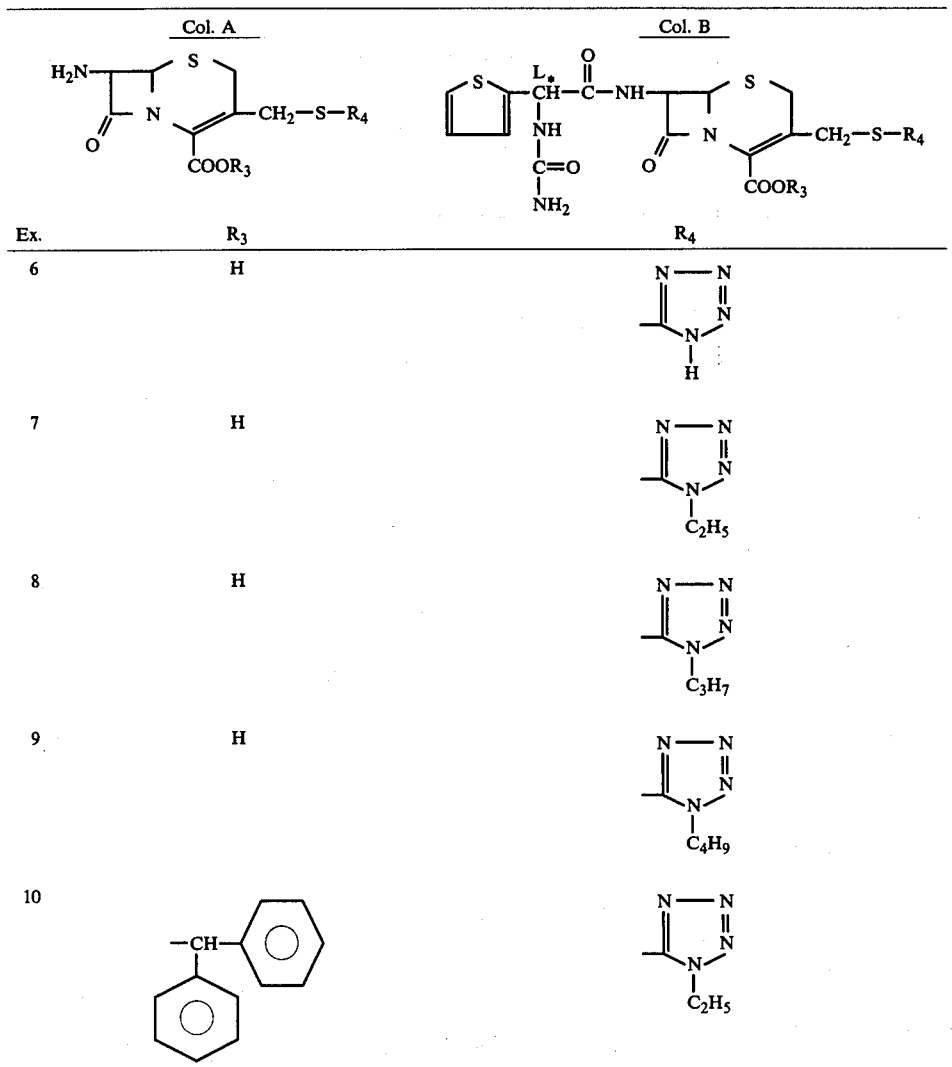

-continued

| | Col. A | Col. B | |
|---|---|---|---|
| Ex. | R₃ | | R₄ |
| 11 | t-C₄H₉ | | 1-methyl-tetrazol-5-yl |
| 12 | —CH₂—C₆H₅ | | 1-methyl-tetrazol-5-yl |
| 13 | —CH₂—(3-Cl-C₆H₄) | | 1-methyl-tetrazol-5-yl |
| 14 | —CH₂—(4-CH₃-C₆H₄) | | 1-ethyl-tetrazol-5-yl |
| 15 | —CH₂—O—C(=O)—CH₃ | | 1-methyl-tetrazol-5-yl |
| 16 | —CH₂—O—C(=O)—CH₂—C₆H₅ | | 1H-tetrazol-5-yl |
| 17 | H | | 1,3,4-thiadiazol-2-yl (H) |
| 18 | H | | 5-ethyl-1,3,4-thiadiazol-2-yl |
| 19 | —CH(C₆H₅)₂ | | 5-propyl-1,3,4-thiadiazol-2-yl |
| 20 | —CH₂—(4-OCH₃-C₆H₄) | | 5-methyl-1,3,4-thiadiazol-2-yl |
| 21 | —CH₂—O—C(=O)—C₂H₅ | | 5-methyl-1,3,4-thiadiazol-2-yl |

-continued

| | Col. A | Col. B | |
|---|---|---|---|
| Ex. | R₃ | | R₄ |
| 22 | —CH₂—O—C(=O)—C₆H₅ | | 5-methyl-1,3,4-thiadiazol-2-yl |
| 23 | H | | 1,3,4-oxadiazol-2-yl |
| 24 | —CH(C₆H₅)₂ | | 5-methyl-1,3,4-oxadiazol-2-yl |
| 25 | H | | 5-methyl-1,3,4-oxadiazol-2-yl |
| 26 | H | | 5-ethyl-1,3,4-oxadiazol-2-yl |
| 27 | —CH₂—O—C(=O)—C₆H₄—Br | | 5-methyl-1,3,4-oxadiazol-2-yl |
| 28 | —CH₂—O—C(=O)—CH₂—C₆H₄—OCH₃ | | 5-methyl-1,3,4-oxadiazol-2-yl |
| 29 | —CH(C₆H₅)₂ | | thiazol-2-yl |
| 30 | —CH(C₆H₅)₂ | | 4-methylthiazol-2-yl |
| 31 | H | | 4-methylthiazol-2-yl |
| 32 | —CH₂—O—C(=O)—CH₃ | | 4-ethylthiazol-2-yl |

-continued

| | Col. A | Col. B | |
|---|---|---|---|
| Ex. | R₃ | | R₄ |
| 33 | —CH(C₆H₅)₂ | | thiadiazole (N=N–N, S) |
| 34 | H | | thiadiazole (N=N–N, S) |
| 35 | t-C₄H₉ | | isothiazole (H, H on S,N ring) |
| 36 | H | | isothiazole-CH₃ |
| 37 | H | | H₃C-isothiazole |
| 38 | H | | isothiazole-C₃H₇ |
| 39 | —CH(C₆H₅)₂ | | isoxazole |
| 40 | H | | isoxazole-CH₃ |
| 41 | H | | H₃C-isoxazole |
| 42 | H | | H₅C₂-isoxazole |
| 43 | —CH(C₆H₅)₂ | | pyridine N-oxide |
| 44 | H | | pyridine N-oxide |

-continued

| | Col. A | Col. B |
|---|---|---|
| Ex. | $R_3$ | $R_4$ |
| 45 | Si(CH$_3$)$_3$ | 1-methyl-tetrazol-5-yl |
| 46 | Sn(CH$_3$)$_3$ | 2-methyl-1,3,4-thiadiazol-5-yl |
| 47 | Si(C$_2$H$_5$)$_3$ | 2-methyl-1,3,4-thiadiazol-5-yl |
| 48 | Sn(C$_2$H$_5$)$_3$ | 1-methyl-tetrazol-5-yl |
| 49 | Ca/2 | 1-methyl-tetrazol-5-yl |
| 50 | Mg/2 | 2-methyl-1,3,4-thiadiazol-5-yl |
| 51 | Na | 2-methyl-1,3,4-thiadiazol-5-yl |
| 52 | Na | 1-methyl-tetrazol-5-yl |
| 53 | Al/3 | 1-methyl-tetrazol-5-yl |
| 54 | [CH$_3$NH$_3$]$^\oplus$ | 1-methyl-tetrazol-5-yl |
| 55 | [(C$_6$H$_5$CH$_2$)$_2$NH$_2$]$^\oplus$ | 2-methyl-1,3,4-thiadiazol-5-yl |

Similarly, by employing the 7-aminocephalosporanic acid of Col. A within the procedures of examples 2 to 5, other compounds within the scope of the invention are obtained.

What is claimed is:
1. An L-isomer compound of the formula:

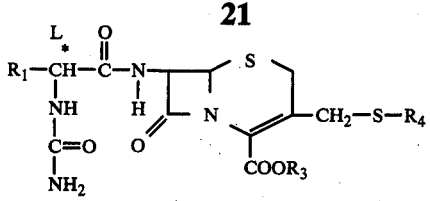

wherein R₁ is 2-thienyl or 3-thienyl; R₃ is hydrogen, sodium or potassium; and R₄ is

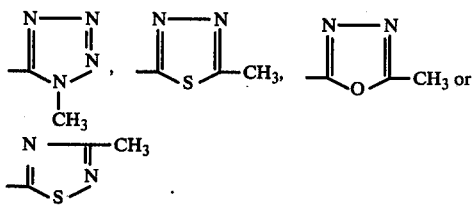

2. An L-isomer compound of the formula:

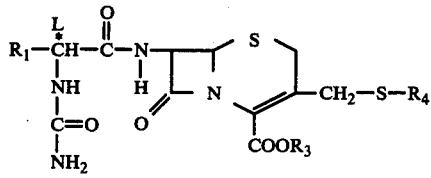

wherein R₁ is 2-furyl or 3-furyl; R₃ is hydrogen, sodium or potassium; and R₄ is

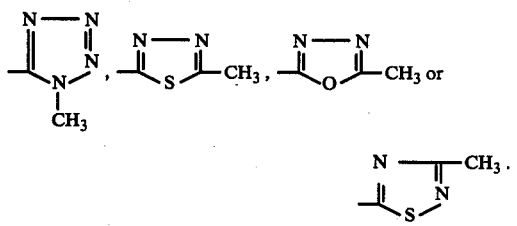

3. An L-isomer compound of the formula:

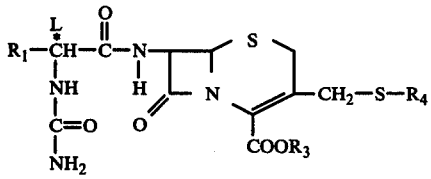

wherein R₁ is phenyl; R₃ is hydrogen, sodium or potassium; and R₄ is

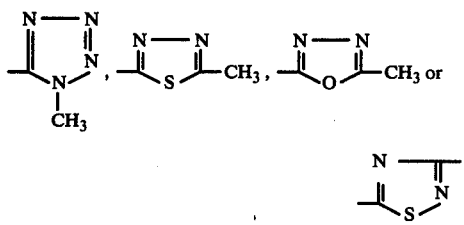

4. The compound of claim 1 wherein R₄ is 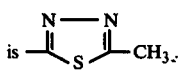

5. The compound of claim 1 wherein R₄ is

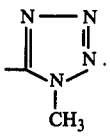

6. The compound of claim 5 wherein R₁ is 2-thienyl.
7. The compound of claim 6, 7β-[[[(aminocarbonyl)-amino](L-2-thienyl)acetyl]amino]-3-[[(1-methyl-1H-tetrazol-5-yl)thio]methyl]-8-oxo-5-thia-1-azabicyclo[4.2.0]oct-2-ene-2-carboxylic acid.
8. The sodium salt of the compound of claim 7.
9. The potassium salt of the compound of claim 7.
10. The compound of claim 5 wherein R₁ is 3-thienyl.
11. The compound of claim 10, 7β-[[[(aminocarbonyl)-amino](L-3thienyl)acetyl]amino]-3-[[(1-methyl-1H-tetrazol-5-yl)thio]methyl]-8-oxo-5-thia-1-azabicyclo[4.2.0]oct-2-ene-2 -carboxylic acid.
12. The sodium salt of the compound of claim 11.
13. The potassium salt of the compound of claim 11.
14. The compound of claim 2 wherein R₄ is

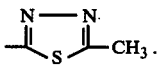

15. The compound of claim 2 wherein R₄ is

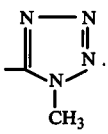

16. The compound of claim 15 wherein R₁ is 2-furyl.
17. The compound of claim 16, 7β-[[[(aminocarbonyl)-amino](L-2-furyl)acetyl]amino]-3-[[(1-methyl-1H-tetrazol-5-yl)thio]methyl]-8-oxo-5-thia-1-azabicyclo[4.2.0]oct-2-ene-2-carboxylic acid.
18. The sodium salt of the compound of claim 17.
19. The potassium salt of the compound of claim 17.
20. The compound of claim 15 wherein R₁ is 3-furyl.
21. The compound of claim 28, 7β-[[[(aminocarbonyl)-amino-](L-3-furyl)acetyl]amino]-3-[[(1-methyl-1H-tetrazol-5-yl)thio]methyl]-8-oxo-5-thia-1-azabicyclo[4.2.0]oct-2-ene-2-carboxylic acid.
22. The sodium salt of the compound of claim 21.
23. The potassium salt of the compound of claim 21.
24. The compound of claim 3 wherein R₄ is

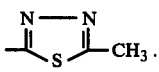

25. The compound of claim 3 wherein R₄ is

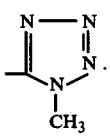

26. The compound of claim 25, 7β-[[[(aminocarbonyl)-amino-](L-phenyl)acetyl]amino]-3-[[(1-methyl-1H-tetrazol-5-yl)thio]methyl]-8-oxo-5-thia-1-azabicyclo[4.2.0]oct-2-ene-2-carboxylic acid.
27. The sodium salt of the compound of claim 26.
28. The potassium salt of the compound of claim 26.

UNITED STATES PATENT AND TRADEMARK OFFICE
CERTIFICATE OF CORRECTION

PATENT NO. : 4,127,716
DATED : November 28, 1978
INVENTOR(S) : Hermann Breuer et al.

It is certified that error appears in the above-identified patent and that said Letters Patent are hereby corrected as shown below:

Column 1, line 34, "of Coo-" should read -- by Coo- --.
Column 2, line 35, "pr 4-bromophenyl" should read -- or 4-bromophenyl --.
Column 8, line 28, "3-thieyl)" should read -- 3-thienyl) --.
Column 10, lines 22 and 23, -- in vacuo -- should be italicized.

Signed and Sealed this

Eleventh Day of March 1980

[SEAL]

Attest:

SIDNEY A. DIAMOND

Attesting Officer

Commissioner of Patents and Trademarks